United States Patent
Takemoto

(10) Patent No.: US 9,265,257 B2
(45) Date of Patent: Feb. 23, 2016

(54) AQUEOUS PEST CONTROL COMPOSITION

(71) Applicant: Sumitomo Chemical Company, Limited, Tokyo (JP)

(72) Inventor: Yukie Takemoto, Hyogo (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 14/312,859

(22) Filed: Jun. 24, 2014

(65) Prior Publication Data

US 2015/0005375 A1  Jan. 1, 2015

(30) Foreign Application Priority Data

Jun. 26, 2013  (JP) ................................. 2013-133587

(51) Int. Cl.
*A01N 53/00* (2006.01)

(52) U.S. Cl.
CPC ...................................... *A01N 53/00* (2013.01)

(58) Field of Classification Search
CPC ...................................................... A01N 53/00
See application file for complete search history.

(56) References Cited

U.S. PATENT DOCUMENTS

| | | |
|---|---|---|
| 2009/0326065 A1 | 12/2009 | Matsumoto et al. |
| 2011/0039698 A1 | 2/2011 | Taranta et al. |
| 2012/0178807 A1 | 7/2012 | Hirayama et al. |
| 2013/0303610 A1 | 11/2013 | Sasaki |

FOREIGN PATENT DOCUMENTS

| | | |
|---|---|---|
| ES | 2390720 A1 | 11/2012 |
| JP | H07-316002 A | 12/1995 |
| JP | 2010-006773 A | 1/2010 |
| JP | 2010-077074 A | 4/2010 |
| JP | 2010-100762 A | 5/2010 |
| JP | 2012-176946 A | 9/2012 |
| WO | 2009074114 A1 | 6/2009 |
| WO | 2012/105424 A1 | 8/2012 |

OTHER PUBLICATIONS

Office Action dated Jun. 11, 2015 in ES App No. 201430953.

*Primary Examiner* — Paul Zarek
(74) *Attorney, Agent, or Firm* — Panitch Schwarze Belisario & Nadel LLP

(57) ABSTRACT

An aqueous pest control composition is provided consisting of: a) 0.01 to 2% by weight of a pyrethroid compound; b) 1 to 40% by weight of polypropylene glycol monopropyl ether which is at least one selected from the group consisting of dipropylene glycol monopropyl ether and tripropylene glycol monopropyl ether; c) 5 to 40% by weight of a water-soluble organic solvent which is at least one selected from the group consisting of glycol monoalkyl ether having 7 or less carbon atoms and glycol having 9 or less carbon atoms; d) 20 to 80% by weight of water; and e) 5% by weight or less of a formulation additive.

6 Claims, No Drawings

AQUEOUS PEST CONTROL COMPOSITION

BACKGROUND OF THE INVENTION

1. Field of the Invention

The present invention relates to an aqueous pest control composition containing a pyrethroid compound.

2. Description of the Related Art

There are conventionally known liquid pest control compositions containing a pyrethroid compound. Moreover, aqueous pest control compositions are known which do not substantially contain a saturated hydrocarbon organic solvent, aromatic hydrocarbon organic solvent, or the like as a solvent (see JP-A-2010-6773 and JP-A-2010-77074).

SUMMARY OF THE INVENTION

As a use of aqueous pest control compositions containing a pyrethroid composition as an effective component and at least water as a solvent, formulations for liquid mosquito repellents or for hand pump sprays are known. Transparent containers may be used as containers for the pest control compositions from the viewpoint of good appearance. In this case, the compositions preferably have high transparency.

Since the pyrethroid compound has low solubility in water, the pyrethroid compound (or a liquid in which a pyrethroid compound is dissolved in an organic solvent) is emulsified (dispersed) in an aqueous solvent in the form of a microdroplet in a composition containing at least water as a solvent. When the particle diameter of the microdroplet is increased after long-term storage, there may be the case where the composition exhibits a state of slight turbidity in appearance and it is therefore desired to develop a pest control composition having high transparency.

The inventors of the present invention have made earnest studies as to an aqueous pest control composition containing a pyrethroid compound, and as a result, found that an aqueous pest control composition having the following composition has excellent long-term storage stability and high transparency. This finding has led to completion of the present invention.

That is, the present invention includes the following inventions.

(Invention 1)

An aqueous pest control composition (hereinafter referred to as "the composition of the present invention") consisting of:
 a) 0.01 to 2% by weight of a pyrethroid compound;
 b) 1 to 40% by weight of polypropylene glycol monopropyl ether (hereinafter referred to as "the propyl ether") which is at least one selected from the group consisting of dipropylene glycol monopropyl ether and tripropylene glycol monopropyl ether;
 c) 5 to 40% by weight of a water-soluble organic solvent (hereinafter referred to as "the water-soluble organic solvent") which is at least one selected from the group consisting of glycol monoalkyl ether having 7 or less carbon atoms and glycol having 9 or less carbon atoms;
 d) 20 to 80% by weight of water; and
 e) 5% by weight or less of a formulation additive.

(Invention 2)

An aqueous pest control composition consisting of:
 a) 0.05 to 1% by weight of a pyrethroid compound;
 b) 10 to 30% by weight of the propyl ether;
 c) 10 to 35% by weight of the water-soluble organic solvent;
 d) 40 to 65% by weight of water; and
 e) 2% by weight or less of a formulation additive.

(Invention 3)

An aqueous pest control composition consisting of:
 a) 0.05 to 1% by weight of a pyrethroid compound;
 b) 15 to 25% by weight of dipropylene glycol monopropyl ether;
 c) 15 to 35% by weight of a water-soluble organic solvent which is at least one selected from the group consisting of triethylene glycol, tripropylene glycol, propylene glycol monoethyl ether, diethylene glycol monopropyl ether, and dipropylene glycol monomethyl ether;
 d) 45 to 55% by weight of water; and
 e) 2% by weight or less of a formulation additive.

(Invention 4)

The aqueous pest control composition according to the invention 1, 2 or 3, wherein c) the water-soluble organic solvent is at least one selected from the group consisting of dipropylene glycol monomethyl ether, propylene glycol monoethyl ether, diethylene glycol monopropyl ether, tripropylene glycol, dipropylene glycol, propylene glycol, diethylene glycol, and triethylene glycol.

The composition of the present invention is superior in long-term storage stability, has high transparency, and is suitable to be used in the form of formulations, which are filled in a transparent container, for liquid mosquito repellents and for hand pump sprays.

DETAILED DESCRIPTION OF THE PREFERRED EMBODIMENTS

The composition of the present invention is an aqueous pest control composition consisting of:
 a) 0.01 to 2% by weight of a pyrethroid compound;
 b) 1 to 40% by weight of the propyl ether;
 c) 5 to 40% by weight of the water-soluble organic solvent;
 d) 20 to 80% by weight of water; and
 e) 5% by weight or less of a formulation additive.

As the pyrethroid compound to be used in the present invention, a commercially available product or a pyrethroid compound produced by a known method may be used.

Examples of the pyrethroid include acrinathrin, allethrin, beta-cyfluthrin, bifenthrin, cycloprothrin, cyfluthrin, cyhalothrin, cypermethrin, empenthrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, meperfluthrin, dimefluthrin, profluthrin, 2,3,5,6-tetrafluoro-4-(methoxymethyl)benzyl=2,2-dimethyl-3-[(1Z)-3,3,3-trifluoro-1-propenyl]cyclopropane carboxylate)(heptafluthrin), 2,3,5,6-tetrafluoro-4-(methoxymethyl)benzyl=2,2,3,3-tetramethylcyclopropanecarboxylate, and 2,3,5,6-tetrafluoro-4-(2-propinyl)benzyl=2,2,3,3-tetramethylcyclopropanecarboxylate.

The composition of the present invention may contain one or more pyrethroid compound.

In the composition of the present invention, the content of the pyrethroid compound is 0.01 to 2% by weight, and preferably 0.05 to 1% by weight.

As the dipropylene glycol monopropyl ether (hereinafter referred to as DPGPE) and tripropylene glycol monopropyl ether (hereinafter referred to as TPGPE), commercially available products or those produced by known methods may be used. A mixture of DPGPE and TPGPE may be used in the composition of the present invention.

In the composition of the present invention, the content of the propyl ether is 1 to 40% by weight, preferably 10 to 30% by weight, and more preferably 15 to 25% by weight.

As the water-soluble organic solvent to be used in the present invention, a commercially available product or one produced by a known method may be used.

The glycol monoalkyl ether in the present invention is a compound represented by the general formula HO-(L-O)$_n$—R and the glycol is a compound represented by the general formula HO-(L-O)$_n$—H (in the general formulas, L represents an alkylene group having 2 to 4 carbon atoms and R represents an alkyl group having 1 to 5 carbon atoms, and n is an integer of 1 to 10).

Examples of the glycol monoalkyl ether having 7 or less carbon atoms include dipropylene glycol monomethyl ether (hereinafter referred to as DPGME), propylene glycol monoethyl ether (hereinafter referred to as PGEE), and diethylene glycol monopropyl ether (hereinafter referred to as DEGPE) and examples of the glycol having 9 or less carbon atoms include tripropylene glycol (hereinafter referred to as TPG), dipropylene glycol (hereinafter referred to as DPG), propylene glycol (hereinafter referred to as PG), diethylene glycol (hereinafter referred to as DEG), and triethylene glycol (hereinafter referred to as TEG). The composition of the present invention may contain one or more water-soluble organic solvent.

In the composition of the present invention, the content of the water-soluble organic solvent is 5 to 40% by weight, preferably 10 to 35% by weight, and more preferably 15 to 35% by weight.

As the water used in the present invention, water such as distilled water or ion exchanged water may be used. The content of the water in the present invention is 20 to 80% by weight, preferably 40 to 65% by weight, and more preferably 45 to 55% by weight.

The composition of the present invention may contain 5% by weight or less and preferably 2% by weight or less of a formulation additive. The formulation additive which may be contained in the present invention is used within the range where the uniformity of the composition of the present invention is not impaired.

Examples of the formulation additive which may be used in the present invention include a thickener, stabilizer, perfume, antiseptic, and synergist.

Examples of the thickener include natural polysaccharides such as xanthan gum, rhamsan gum, locust bean gum, carrageenan, and welan gum; synthetic polymers such as sodium polyacrylates; and semi-synthetic polymers such as carboxymethyl cellulose.

Examples of the stabilizer include BHT (2,6-di-t-butyl-4-methylphenol), BHA (mixture of 2-t-butyl-4-methoxyphenol and 3-t-butyl-4-methoxyphenol), vitamin C, and catechin.

Examples of the perfume include natural perfumes, synthetic perfumes, and extracted perfumes.

Examples of the antiseptic include benzoic acid, sodium benzoate, methyl paraoxybenzoate, butyl paraoxybenzoate, isopropyl methylphenol, benzalkonium chloride, chlorhexidine hydrochloride, hydrogen peroxide water, chlorhexidine gluconate, salicylic acid, sodium salicylate, zinc pyrithione, sorbic acid, potassium sorbate, dehydroacetic acid, sodium dehydroacetate, phenoxyethanol, isothiazoline derivatives such as 5-chloro-2-methyl-4-isothiazolin-3-one and 2-methyl-4-isothiazolin-3-one, 2-bromo-2-nitropropane-1,3-diol, and salicylic acid derivatives. Specific examples include BIOHOPE L (manufactured by KI Chemical Industry Co., Ltd.) and Proxel GXL (manufactured by Avecia Co., Ltd.).

Examples of the synergist include piperonyl butoxide, sesamex, sulfoxide, N-(2-ethylhexyl)-8,9,10-trinorborn-5-ene-2,3-dicarboximide (MGK 264), N-declyimidazole, WARF-antiresistant, TBPT, TPP, IBP, PSCP, methyl iodide (CH$_3$I), t-phenylbutenone, diethyl maleate, DMC, FDMC, ETP, ETN, and d-limonene.

In a method for producing the composition of the present invention, the components a, b, c, d, and e may be properly mixed in a container equipped with a stirrer to thereby produce the composition.

For example, the composition of the present invention may be used as formulations for heat transpiration apparatuses such as liquid mosquito repellents. The composition may be also used as formulations for spraying apparatuses such as an ultrasonic atomizer and pump spray.

The composition of the present invention is preferably used in the form of a heat transpiration agent or composition for an ultrasonic atomizer.

Examples of pests which can be controlled by the composition of the present invention include arthropods such as insects and mites and specifically include the following pests and the like.

Lepidoptera pests: Pyralidae such as *Chilo suppressalis, Cnaphalocrocis medinalis,* and *Plodia interpunctella*; cabbage moths such as *Spodoptera litura, Pseudaletia separata,* and *Mamestra brassicae*; Pieridae such as *Pieris rapae*; Tortricidae such as *Adoxophyes* spp.; Carposinidae; Lyonetiidae; Lymantriidae; Plusiinae; *Agrotis* spp. such as *Agrotis segetum* and *Agrotis ipsilon; Helicoverpa* spp.; *Heliothis* spp.; *Plutella xylostella; Parnara guttata; Tinea translucens*; and *Tineola bisselliella*

Diptera pests: *Culex* spp. such as *Culex pipiens pallens, Culex tritaeniorhynchus,* and *Culex quinquefasciatus; Aedes* spp. Such as *Aedes aegypti* and *Aedes albopictus; Anopheles* spp. such as *Anopheles sinensis* and *Anopheles gambiae*; Chironomidae; Muscidae such as *Musca domestica, Muscina stabulans,* and *Fannia canicularis*; Calliphoridae; Sarcophagidae; Anthomyiidae such as *Delia platura* and *Delia antique*; Tephritidae; Drosophilidae; Psychodidae; Phoridae; Tabanidae; Simuliidae; Stomoxyidae; and Ceratopogonidae;

Dictyoptera pests: *Blattella germanica; Periplaneta fuliginosa; Periplaneta Americana; Periplaneta australasiae; Periplaneta brunnea*; and *Blatta orientalis;*

Hymenoptera pests: Formicidae; Hymenoptera (for example, *Polistes hebraeus* such as *Polistes chinensis, Polistesriparius, Polistes jokahamae, Polistes nipponensis, Polistes snelleni,* and *Polistes japonicas*; Vespidae such as *Vespa mandarinia japonica, Vespa simillima xanthoptera, Vespa analis Fabricius, Vespa crabro, Vespa ducalis, Vespula flaviceps, Vespula shidai ishikawa,* and *Dolichovespula media*; Bethylidae; Xylocopa; Pompilidae; Sphecidae; and Eumeninae);

Siphonnaptera pests: *Ctenocephalides canis; Ctenocephalides felis*; and *Pulex irritans;*

Anoplura pests: *Pediculus humanus; Pthirus pubis; Pediculus humanus capitis*; and *Pediculus humanus corporis;*

Isoptera pests: *Reticulitermes speratus* and *Coptotermes formosanus;*

Hemiptera pests: Delphacidae such as *Laodelphax striatellus, Nilaparvata lugens,* and *Sogatella furcifera*; Deltocephalidae such as *Nephotettix cincticeps* and *Nephotettix virescens*; Aphididae; Pentatomidae; Aleyrodidae; Scales; Tingidae; Psyllidae; and Cimicidae;

Coleoptera pests: *Attagenus japonicas; Authrenus verbasci*; corn rootworms such as *Diabrotica virgifera* and *Diabrotica undecimpunctata howardi*; Scarabaeidae such as *Anomala cuprea* and *Anomala rufocuprea*; Curculionidae such as *Sitophilus zeamais, Lissorhoptrus oryzophilus, Anthonomus grandis*, and *Callosobruchus chinensis*; Tenebrionidae such as *Tenebrio molitor* and *Tribolium castaneum*; Chrysomelidae such as *Oulema oryzae, Phyllotreta striolata*, and *Aulacophora femoralis*; Anobiidae; *Epilachna* spp. such as *Epilachna vigintioctopunctata*; Lyctidae; Bostrychidae; Cerambycidae; and *Paederus fuscipes*;

Thysanoptera pests: *Thrips parmi; Flankliniella occidentalis*; and *Thrips hawaiiensis*;

Orthoptera pests; Gryllotalpidae and Acrididae;

Acarina pests: Dermanyssidae such as *Dermatophagoides farinae* and *Dermatophagoides ptrenyssnus*; Acaridae such as *Tyrophagus putrescentiae* and *Aleuroglyphus ovatus*; Glycyphagidae such as *Glycyphagus privates, Glycyphagus domesticus*, and *Glycyphagus destructor*; Cheyletidae such as *Cheyletus malaccensis* and *Cheyletus fortis*; Tarsonemidae; *Chortoglyphus* spp.; *Haplochthonius simplex*; Tetranychidae such as *Tetranychus urticae, Tetranychus kanzawai, Panonychus citri*, and *Panonychus ulmi*; and Ixodidae such as *Haemaphysalis longiconis*.

A pest control method according to the present invention is usually carried out by applying the composition of the present invention to pests or habitats of pests.

Examples of a method for applying the composition of the present invention include the following methods. The application method may be properly selected depending on the form, use place, etc. of the composition of the present invention.

(1) A method in which the composition of the present invention is used in the form of a heat transpiration agent to transpire the composition on habitats of pests.

(2) A method in which the composition of the present invention is sprayed on pests or habitats of pests by using a spraying apparatus such as an ultrasonic atomizer, an aerosol system or pump spraying apparatus.

In this case, the amount and concentration of the compound to be applied may be each properly determined depending on, for example, the form, application time, application place, and application method of the composition of the present invention, the kinds of pest, and damage situation.

In the pest control method of the present invention, an example of a method for applying the composition of the present invention by using the composition in the form of a heat transpiration agent includes a method in which a part of a porous liquid absorption core is immersed in the composition of the present invention to allow the core to absorb the composition, and then the upper part of the core is heated to transpire the composition absorbed as a liquid. As a heat transpiration type insecticidal apparatus, those well-known in the art may be used. For example, the heat transpiration type insecticidal apparatus described in JP-B-2-25885 may be used.

As a porous material which is the material used for the liquid absorption core, there are used those obtained by binding, for example, an inorganic powder such as clay, talc, kaolin, diatomaceous earth, gypsum, perlite, bentonite, acid clay, glass fiber, or asbestos with a binder such as carboxymethyl cellulose, starch, gum arabic, gelatin, or polyvinyl alcohol, followed by molding; those obtained by forming an inorganic material such as clay, talc, bentonite, alumina, or silica into a core form by solidification, followed by calcining; those obtained by molding a resin into a core form; those obtained by binding glass fibers into a bundle; and the like.

In the pest control method of the present invention, an example of a method for applying the composition of the present invention in the case of applying the composition of the present invention by using an ultrasonic atomizer includes a method in which the composition of the present invention is sprayed using an ultrasonic atomizer. In this case, the composition of the present invention is atomized by ultrasonic wave and then sprayed. As the ultrasonic atomizer to be used in this method, the ultrasonic atomizer described in JP-A-2009-118792 may be used.

In the pest control method of the present invention, an example of a method for applying the composition of the present invention by using a pump spray includes a method in which a pump spray (a sprayer which needs no propellant and sprays the composition by the action of a pump) filled with the composition of the present invention is used to spray the composition. As the pump spray to be used in this method, those well-known in the art may be used, and for example, the pump spray described in JP-A-8-295359 or a trigger type pump spray described in JP-A-2002-233798 may be used.

EXAMPLES

Next, the present invention will be described in more detail by way of formulation examples and test examples; however, the present invention is not limited thereto.

First, formulation examples of the composition of the present invention will be shown. In these examples, all parts indicate parts by weight, unless otherwise noted.

Formulation Example 1

An aqueous pest control composition was obtained by thoroughly mixing under stirring 0.6 parts by weight of prallethrin, 19.4 parts by weight of DPGPE, 10.0 parts by weight of TEG, 20.0 parts by weight of PGEE, and 50.0 parts by weight of water.

Formulation Example 2

An aqueous pest control composition was obtained by thoroughly mixing under stirring 0.6 parts by weight of profluthrin, 19.4 parts by weight of DPGPE, 10.0 parts by weight of TEG, 20.0 parts by weight of PGEE, and 50.0 parts by weight of water.

Formulation Example 3

An aqueous pest control composition was obtained by thoroughly mixing under stirring 0.3 parts by weight of dimefluthrin, 19.7 parts by weight of DPGPE, 30.0 parts by weight of PGEE, and 50.0 parts by weight of water.

Formulation Example 4

An aqueous pest control composition was obtained by thoroughly mixing under stirring 0.3 parts by weight of dimefluthrin, 19.7 parts by weight of DPGPE, 20.0 parts by weight of DEGPE, and 60.0 parts by weight of water.

Formulation Example 5

An aqueous pest control composition was obtained by thoroughly mixing under stirring 0.3 parts by weight of dimefluthrin, 19.7 parts by weight of DPGPE, 30.0 parts by weight of TPG, and 50.0 parts by weight of water.

Formulation Example 6

An aqueous pest control composition was obtained by thoroughly mixing under stirring 0.3 parts by weight of dimefluthrin, 19.7 parts by weight of DPGPE, 10.0 parts by weight of TEG, 20.0 parts by weight of PGEE, and 50.0 parts by weight of water.

Formulation Example 7

An aqueous pest control composition was obtained by thoroughly mixing under stirring 0.3 parts by weight of dimefluthrin, 19.7 parts by weight of DPGPE, 10.0 parts by weight of TEG, 20.0 parts by weight of DPGME, and 50.0 parts by weight of water.

Formulation Example 8

An aqueous pest control composition was obtained by thoroughly mixing under stirring 0.3 parts by weight of dimefluthrin, 19.7 parts by weight of DPGPE, 15.0 parts by weight of TEG, 15.0 parts by weight of DPGME, and 50.0 parts by weight of water.

Formulation Example 9

An aqueous pest control composition was obtained by thoroughly mixing under stirring 0.6 parts by weight of meperfluthrin, 19.4 parts by weight of DPGPE, 10.0 parts by weight of TEG, 20.0 parts by weight of PGEE, and 50.0 parts by weight of water.

Formulation Example 10

An aqueous pest control composition is obtained by thoroughly mixing under stirring 0.6 parts by weight of prallethrin, 19.4 parts by weight of DPGPE, 10.0 parts by weight of TEG, 20.0 parts by weight of PGEE, 0.3 parts by weight of piperonyl butoxide, and 49.7 parts by weight of water.

Formulation Example 11

An aqueous pest control composition is obtained by thoroughly mixing under stirring 0.6 parts by weight of prallethrin, 19.4 parts by weight of DPGPE, 10.0 parts by weight of TEG, 20.0 parts by weight of PGEE, 0.1 parts by weight of BHT, and 49.9 parts by weight of water.

Formulation Example 12

An aqueous pest control composition is obtained by thoroughly mixing under stirring 0.6 parts by weight of dimefluthrin, 19.4 parts by weight of DPGPE, 10.0 parts by weight of TEG, 20.0 parts by weight of PGEE, 0.3 parts by weight of piperonyl butoxide, and 49.7 parts by weight of water.

Formulation Example 13

An aqueous pest control composition is obtained by thoroughly mixing under stirring 0.6 parts by weight of meperfluthrin, 19.4 parts by weight of DPGPE, 10.0 parts by weight of TEG, 20.0 parts by weight of PGEE, 0.3 parts by weight of piperonyl butoxide, and 49.7 parts by weight of water.

Formulation Example 14

An aqueous pest control composition was obtained by thoroughly mixing under stirring 0.4 parts by weight of dimefluthrin, 19.6 parts by weight of DPGPE, 10.0 parts by weight of TEG, 20.0 parts by weight of PGEE, and 50.0 parts by weight of water.

Formulation Example 15

An aqueous pest control composition was obtained by thoroughly mixing under stirring 0.3 parts by weight of dimefluthrin, 29.7 parts by weight of DPGPE, 20.0 parts by weight of TPG, and 50.0 parts by weight of water.

Formulation Example 16

An aqueous pest control composition was obtained by thoroughly mixing under stirring 0.3 parts by weight of dimefluthrin, 19.7 parts by weight of TPGPE, 30.0 parts by weight of PGEE, and 50.0 parts by weight of water.

Formulation Example 17

An aqueous pest control composition was obtained by thoroughly mixing under stirring 0.3 parts by weight of dimefluthrin, 19.7 parts by weight of TPGPE, 30.0 parts by weight of TPG, and 50.0 parts by weight of water.

Formulation Example 18

An aqueous pest control composition was obtained by thoroughly mixing under stirring 0.3 parts by weight of dimefluthrin, 10.7 parts by weight of DPGPE, 39.0 parts by weight of PGEE, and 50.0 parts by weight of water.

Formulation Example 19

An aqueous pest control composition was obtained by thoroughly mixing under stirring 0.3 parts by weight of dimefluthrin, 10.7 parts by weight of DPGPE, 29.0 parts by weight of DEGPE, and 60.0 parts by weight of water.

Formulation Example 20

An aqueous pest control composition was obtained by thoroughly mixing under stirring 0.3 parts by weight of dimefluthrin, 10.7 parts by weight of DPGPE, 10.0 parts by weight of TEG, 29.0 parts by weight of PGEE, and 50.0 parts by weight of water.

Formulation Example 21

An aqueous pest control composition was obtained by thoroughly mixing under stirring 0.3 parts by weight of dimefluthrin, 10.7 parts by weight of TPGPE, 39 parts by weight of PGEE, and 50.0 parts by weight of water.

Formulation Example 22

An aqueous pest control composition was obtained by thoroughly mixing under stirring 0.3 parts by weight of dimefluthrin, 10.7 parts by weight of TPGPE, 10.0 parts by weight of TEG, 29.0 parts by weight of PGEE, and 50.0 parts by weight of water.

Formulation Example 23

An aqueous pest control composition was obtained by thoroughly mixing under stirring 0.3 parts by weight of dimefluthrin, 14.7 parts by weight of TPGPE, 10.0 parts by weight of TEG, 25.0 parts by weight of PGEE, and 50.0 parts by weight of water.

Next, formulation examples of aqueous pest control compositions each of which is different from the composition of the present invention will be described.

Comparative Formulation Example 1

An aqueous pest control composition was obtained by thoroughly mixing under stirring 0.6 parts by weight of prallethrin, 29.4 parts by weight of propylene glycol monopropyl ether (hereinafter referred to as PGPE), 15.0 parts by weight of TEG, and 55.0 parts by weight of water.

Comparative Formulation Example 2

An aqueous pest control composition was obtained by thoroughly mixing under stirring 0.6 parts by weight of prallethrin, 34.2 parts by weight of PGPE, 15.0 parts by weight of TEG, and 50.0 parts by weight of water.

Comparative Formulation Example 3

An aqueous pest control composition was obtained by thoroughly mixing under stirring 0.6 parts by weight of profluthrin, 29.4 parts by weight of PGPE, 15.0 parts by weight of TEG, and 55.0 parts by weight of water.

Next, the appearance of each aqueous pest control composition was observed after the aqueous pest control composition was stored at 25° C. or 54° C. for 3 hours to confirm that the composition of the present invention is superior in storage stability and has high transparency.

TABLE 1

|  | Results of Observation of Appearance | |
| --- | --- | --- |
|  | 25° C. | 54° C. |
| Formulation Example 1 | Transparent | Transparent |
| Formulation Example 2 | Transparent | Transparent |
| Formulation Example 3 | Transparent | Transparent |
| Formulation Example 4 | Transparent | Transparent |
| Formulation Example 5 | Transparent | Transparent |
| Formulation Example 6 | Transparent | Transparent |
| Formulation Example 7 | Transparent | Transparent |
| Formulation Example 8 | Transparent | Transparent |
| Formulation Example 9 | Transparent | Transparent |
| Formulation Example 14 | Transparent | Transparent |
| Formulation Example 15 | Transparent | Transparent |
| Formulation Example 16 | Transparent | Transparent |
| Formulation Example 17 | Transparent | Transparent |
| Formulation Example 18 | Transparent | Transparent |
| Formulation Example 19 | Transparent | Transparent |
| Formulation Example 20 | Transparent | Transparent |
| Formulation Example 21 | Transparent | Transparent |
| Formulation Example 22 | Transparent | Transparent |
| Formulation Example 23 | Transparent | Transparent |
| Comparative Formulation Example 1 | Clouded | Clouded |
| Comparative Formulation Example 2 | Transparent | Clouded |
| Comparative Formulation Example 3 | Clouded | Clouded |

The composition of the present invention is superior in long-term storage stability, has high transparency, is suitably used in the form of the formulation filled in a transparent container, and is therefore useful.

What is claimed is:

1. An aqueous pest control composition consisting of:
   a) 0.01 to 2% by weight of a pyrethroid compound;
   b) 1 to 40% by weight of polypropylene glycol monopropyl ether which is at least one selected from the group consisting of dipropylene glycol monopropyl ether and tripropylene glycol monopropyl ether;
   c) 5 to 40% by weight of a water-soluble organic solvent which is at least one selected from the group consisting of glycol monoalkyl ether having 7 or less carbon atoms and glycol having 9 or less carbon atoms;
   d) 20 to 80% by weight of water; and
   e) 5% by weight or less of a formulation additive.

2. An aqueous pest control composition consisting of:
   a) 0.05 to 1% by weight of a pyrethroid compound;
   b) 10 to 30% by weight of polypropylene glycol monopropyl ether which is at least one selected from the group consisting of dipropylene glycol monopropyl ether and tripropylene glycol monopropyl ether;
   c) 10 to 35% by weight of a water-soluble organic solvent which is at least one selected from the group consisting of glycol monoalkyl ether having 7 or less carbon atoms and glycol having 9 or less carbon atoms;
   d) 40 to 65% by weight of water; and
   e) 2% by weight or less of a formulation additive.

3. An aqueous pest control composition consisting of:
   a) 0.05 to 1% by weight of a pyrethroid compound;
   b) 15 to 25% by weight of dipropylene glycol monopropyl ether;
   c) 15 to 35% by weight of a water-soluble organic solvent which is at least one selected from the group consisting of triethylene glycol, tripropylene glycol, propylene glycol monoethyl ether, diethylene glycol monopropyl ether, and dipropylene glycol monomethyl ether;
   d) 45 to 55% by weight of water; and
   e) 2% by weight or less of a formulation additive.

4. The aqueous pest control composition according to claim 1, wherein c) the water-soluble organic solvent is at least one selected from the group consisting of:
   dipropylene glycol monomethyl ether;
   propylene glycol monoethyl ether;
   diethylene glycol monopropyl ether;
   tripropylene glycol;
   dipropylene glycol;
   propylene glycol;
   diethylene glycol; and
   triethylene glycol.

5. The aqueous pest control composition according to claim 2, wherein c) the water-soluble organic solvent is at least one selected from the group consisting of:
   dipropylene glycol monomethyl ether;
   propylene glycol monoethyl ether;
   diethylene glycol monopropyl ether;
   tripropylene glycol;
   dipropylene glycol;
   propylene glycol;
   diethylene glycol; and
   triethylene glycol.

6. The aqueous pest control composition according to claim 3, wherein c) the water-soluble organic solvent is at least one selected from the group consisting of:
   dipropylene glycol monomethyl ether;
   propylene glycol monoethyl ether;
   diethylene glycol monopropyl ether;
   tripropylene glycol;
   dipropylene glycol;
   propylene glycol;
   diethylene glycol; and
   triethylene glycol.

* * * * *